US011510475B2

(12) United States Patent
McMahon

(10) Patent No.: US 11,510,475 B2
(45) Date of Patent: Nov. 29, 2022

(54) DEVICE FOR APPLYING A PRODUCT

(71) Applicant: MITCHELL TERRACE PTY. LTD., Melbourne (AU)

(72) Inventor: Anthony Dominic McMahon, Camberwell (AU)

(73) Assignee: MITCHELL TERRACE PTY. LTD, Melbourne (AU)

( * ) Notice: Subject to any disclaimer, the term of this patent is extended or adjusted under 35 U.S.C. 154(b) by 345 days.

(21) Appl. No.: 15/741,894

(22) PCT Filed: Jul. 6, 2016

(86) PCT No.: PCT/AU2016/050587
§ 371 (c)(1),
(2) Date: Jan. 4, 2018

(87) PCT Pub. No.: WO2017/004673
PCT Pub. Date: Jan. 12, 2017

(65) Prior Publication Data
US 2018/0192761 A1 Jul. 12, 2018

(30) Foreign Application Priority Data
Jul. 6, 2015 (AU) ................................ 2015902652

(51) Int. Cl.
*A61M 1/06* (2006.01)
*A45D 34/04* (2006.01)
(Continued)

(52) U.S. Cl.
CPC ........... *A45D 34/04* (2013.01); *A61M 35/003* (2013.01); *A45D 2034/005* (2013.01); *A45D 2200/155* (2013.01)

(58) Field of Classification Search
CPC .............. A45D 34/04; A45D 2034/005; A45D 2200/155; A45D 44/00; A45D 2200/054;
(Continued)

(56) References Cited

U.S. PATENT DOCUMENTS

2010/0262051 A1* 10/2010 De Laforcade ........ A45D 34/04
601/84
2011/0025997 A1 2/2011 Ebihara
(Continued)

FOREIGN PATENT DOCUMENTS

EP 3133956 A2 3/2017
KR 20100019181 A * 4/2003
(Continued)

OTHER PUBLICATIONS

Collins English Dictionary—Complete and Unabridged, 12th Edition 2014 (Year: 2014).*
(Continued)

*Primary Examiner* — Tatyana Zalukaeva
*Assistant Examiner* — Ilya Y Treyger
(74) *Attorney, Agent, or Firm* — David Nocilly

(57) ABSTRACT

A device for applying a product onto skin having a housing which receives the product from a container (12) and receives a gas. The housing has an outlet through which the product and gas are dispensed onto an area of the skin, and a heater configured to heat the gas and/or the product such that the gas and/or product is applied to the skin in a heated state. The product meets the gas adjacent to the outlet where the gas collects the product such that the heated gas and product are projected through the outlet and applied to the skin in a heated state. The housing forms a handheld device to be held by a user and moved across the skin to apply the product.

20 Claims, 6 Drawing Sheets

(51) Int. Cl.
   *A61M 35/00* (2006.01)
   *A61M 31/00* (2006.01)
   *A61M 37/00* (2006.01)
   *A61M 1/00* (2006.01)
   *A61M 5/00* (2006.01)
   *A61M 5/178* (2006.01)
   *A61M 25/00* (2006.01)
   *A45D 34/00* (2006.01)

(58) Field of Classification Search
   CPC ..... A45D 34/00; A61M 35/003; A61M 35/30; A61M 35/00
   See application file for complete search history.

(56) References Cited

U.S. PATENT DOCUMENTS

2011/0137268 A1    6/2011  Thomason et al.
   2013/0330285 A1*  12/2013  Smart ............... A61M 35/00 424/59
   2014/0219701 A1*   8/2014  Eberlein ............ A45D 34/04 401/2
   2014/0234004 A1*   8/2014  Thorpe ............. A45D 40/26 401/1

FOREIGN PATENT DOCUMENTS

KR    20100019181 A  *  2/2010
   WO    2012/116244       8/2012
   WO    2014168298 A2   10/2014
   WO    2015162430 A2   10/2015

OTHER PUBLICATIONS

International Search Report Form PCT/IPEA/416, International Application No. PCT/AU2016/050587, pp. 1-10, dated Sep. 1, 2016.

* cited by examiner

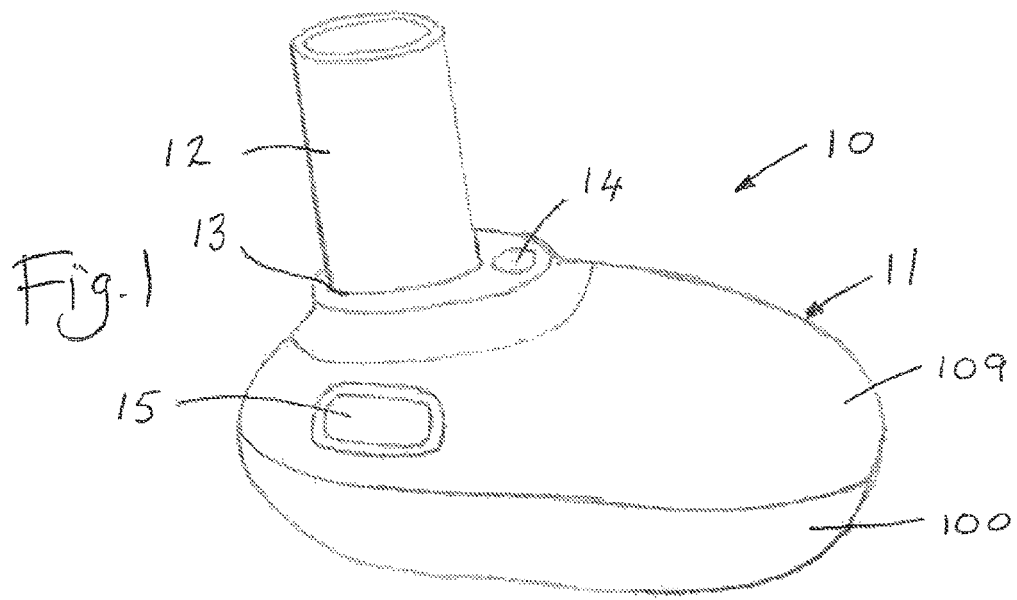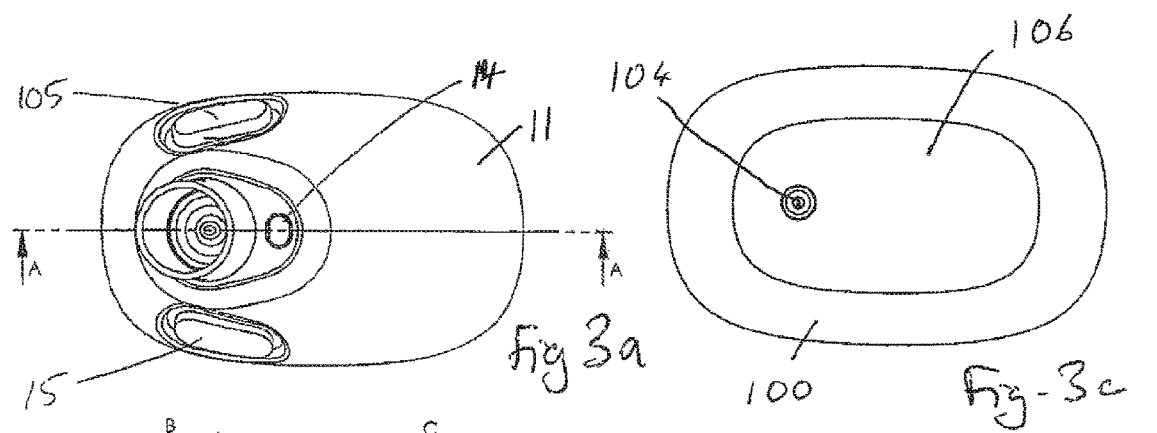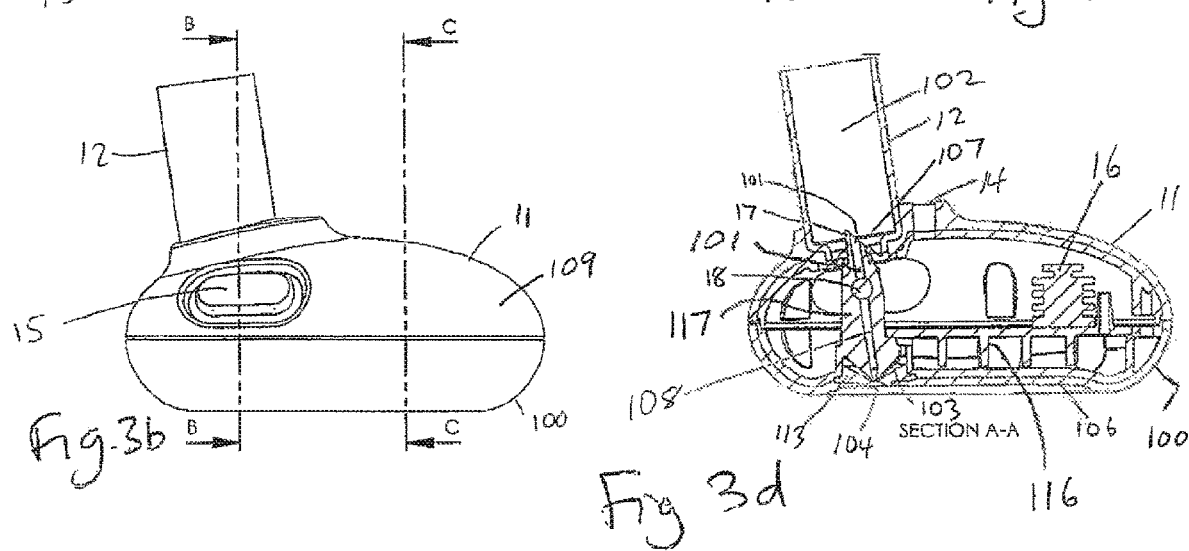

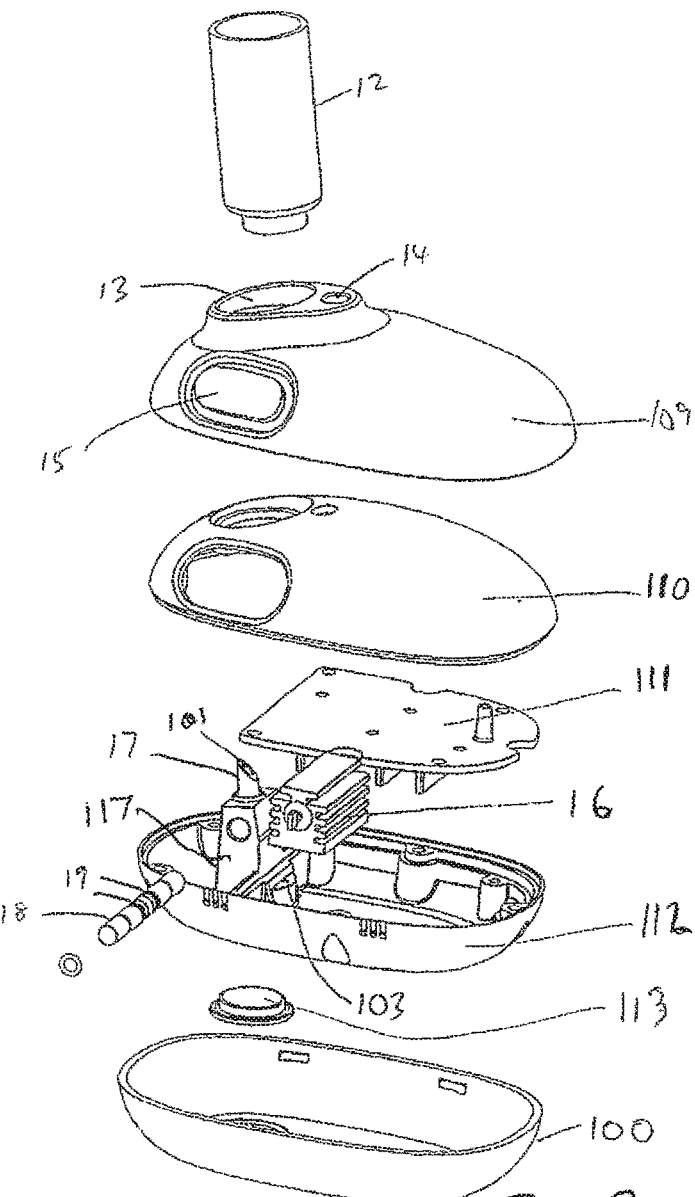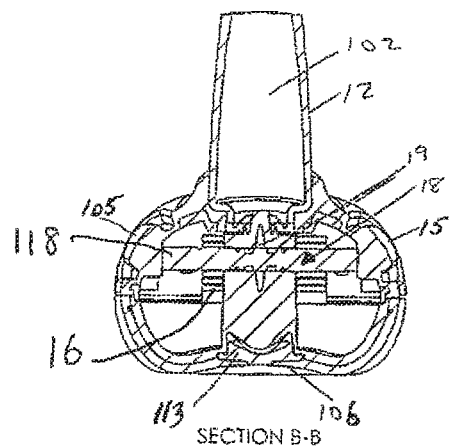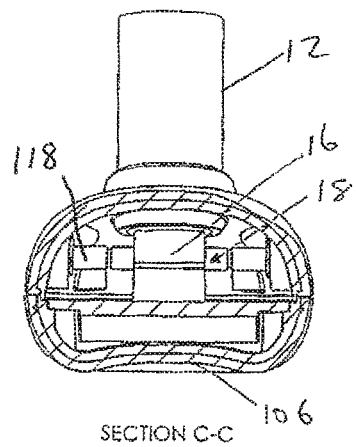

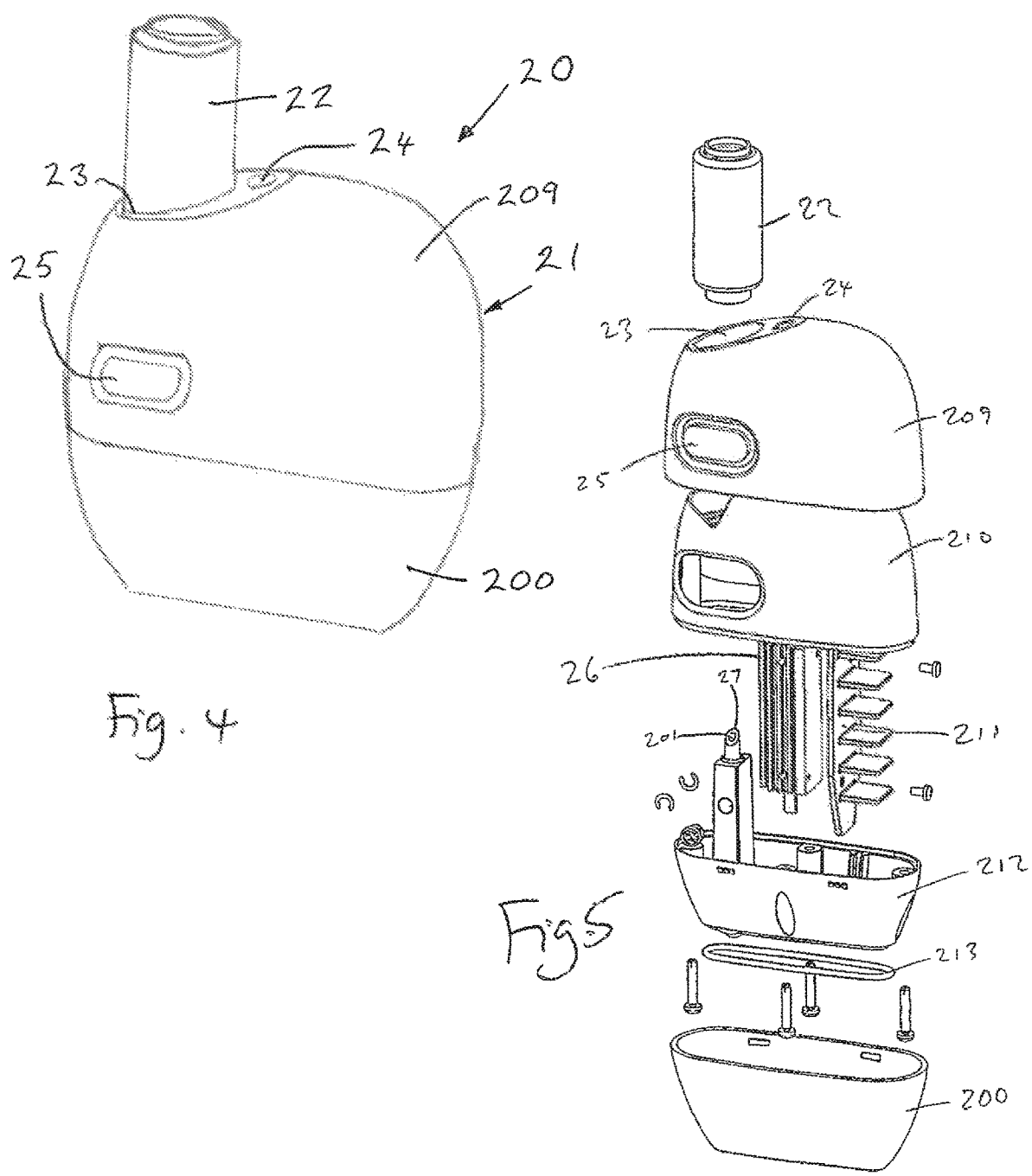

SECTION A-A

SECTION B-B

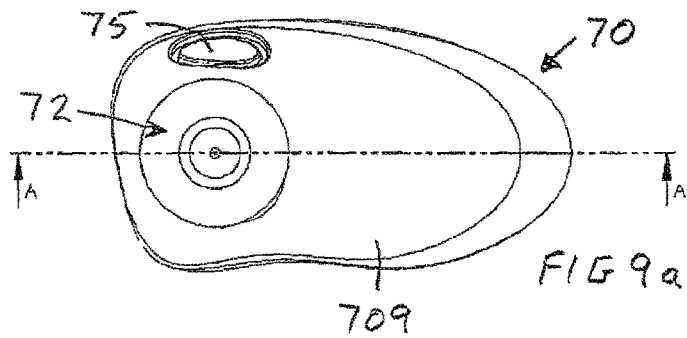
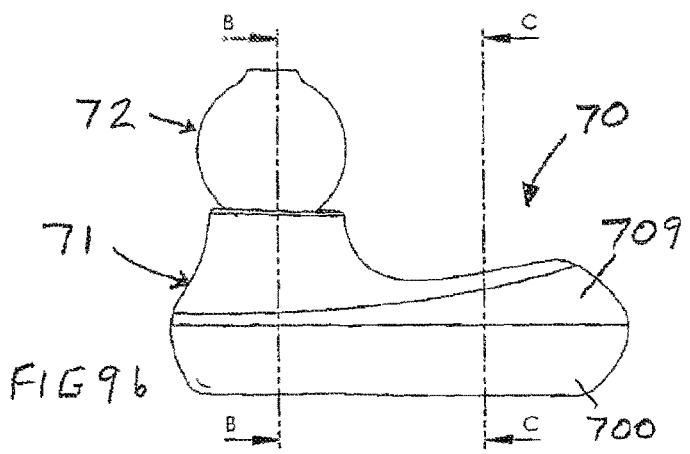
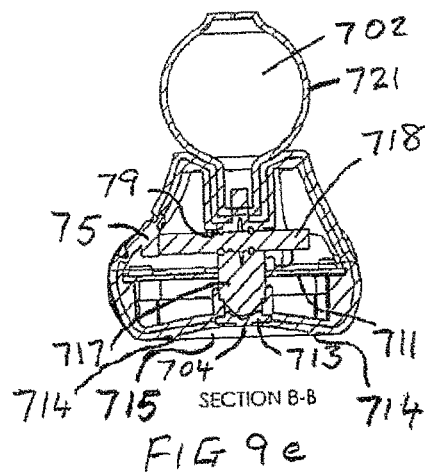
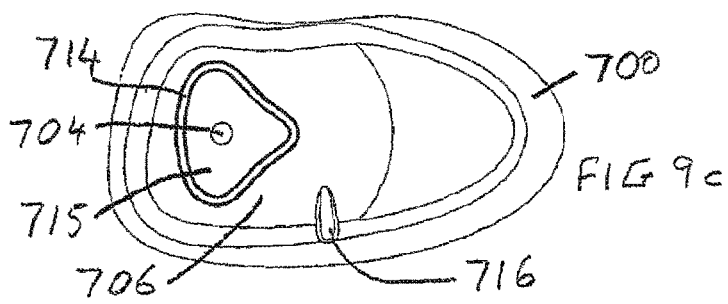
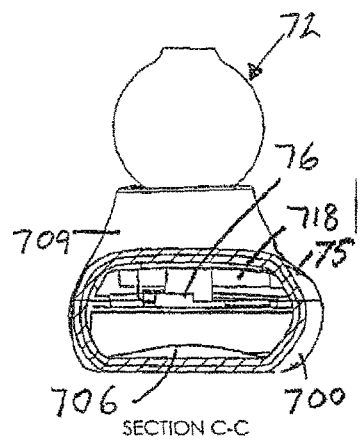
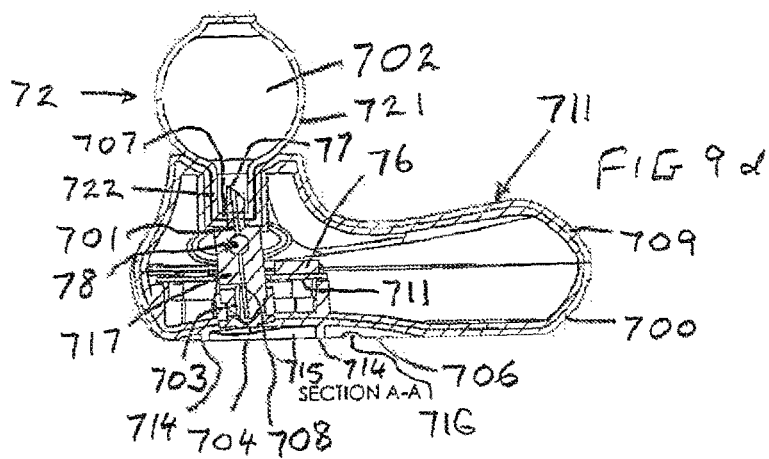

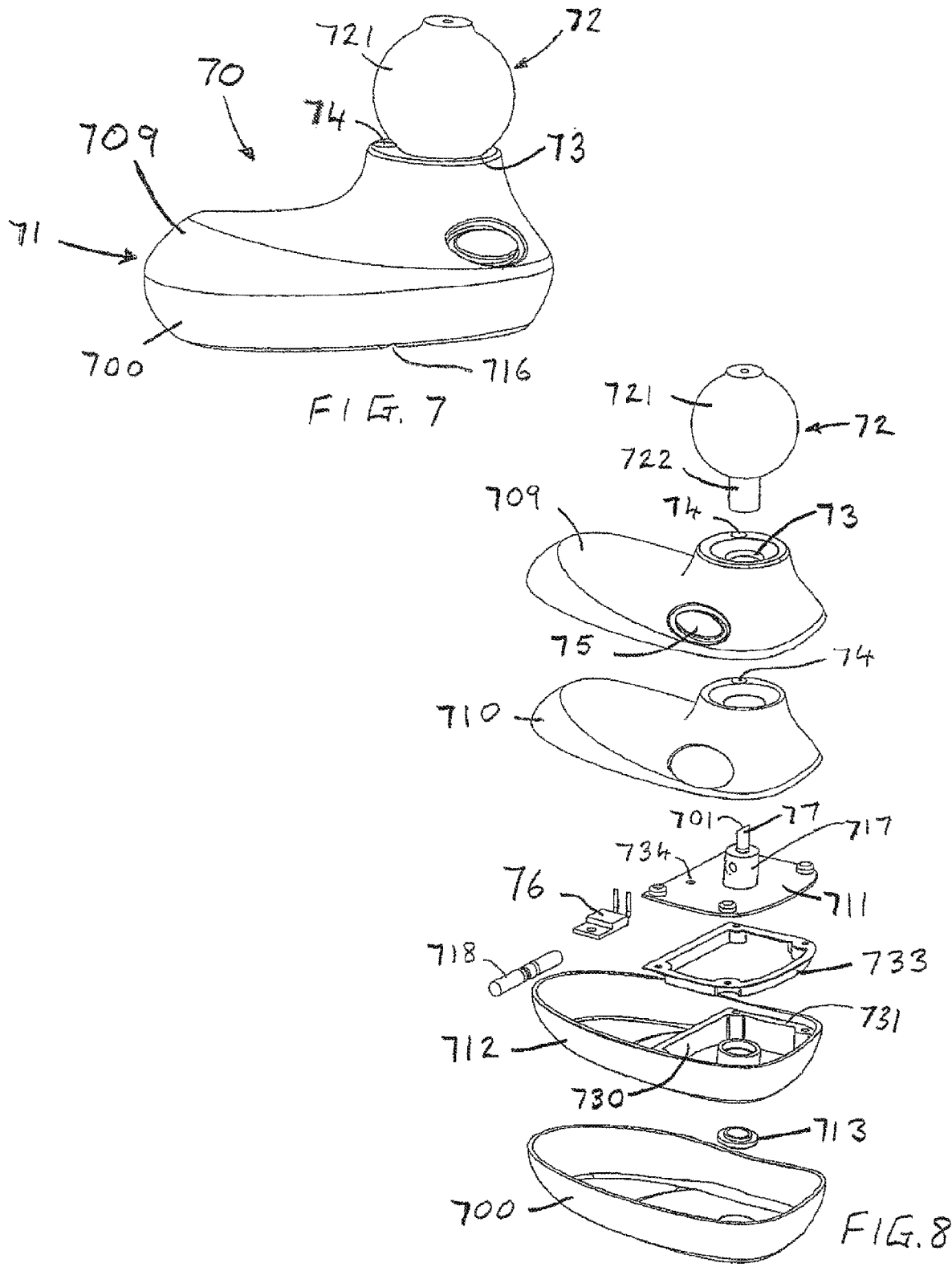

DEVICE FOR APPLYING A PRODUCT

FIELD OF THE INVENTION

The present invention relates to a device for applying a product, such as a therapeutic or cosmetic product, to the skin of a human or animal.

BACKGROUND TO THE INVENTION

Beauty treatments have developed over the years to a point where consumers expect more than just the application of a cream to their skin. There has been an increased demand for professional quality beauty treatments which provide skin enhancing effects, such as rejuvenating, anti-aging and hydrating. However, some treatments, such as botulinum toxin, a neurotoxic protein used for medical and cosmetic purposes, often sold under the registered trade mark BOTOX®, are invasive. These invasive treatments require the injection of the product into the skin using a syringe and usually involve a recovery period following the treatment.

Treatments are now available which use machines that aid in applying various lotions to the skin non-invasively. These treatments have an advantage over invasive treatments because they do not puncture the skin or require a recovery period following the treatment.

One such treatment uses oxygen under low pressure to aid in the delivery of ingredients within a serum to the skin, which increases the absorption of the serum into the skin. These machines have an applicator with a pen-sized 'airbrush' head. The oxygen is pressurised by a machine and sent through a tube to the applicator where it collects the serum and is projected onto the skin.

It is desirable to provide a device for the application of a product that is more comfortable to a user and/or that has an improved absorption of the product and/or that provides the public with a useful choice.

SUMMARY OF THE INVENTION

An aspect of the present invention broadly consists in a device for applying a product onto skin, the device comprising:
a housing for receiving the product and a gas;
one or more outlets in the housing through which the product and gas is dispensed onto an area of the skin; and
at least one heater arranged or configured to heat the gas such that the gas is applied to the skin in a heated state and/or to heat the product such that the product is applied to the skin in a heated state.

The device may include one or more heaters, at least one of which is preferably positioned within the housing. It is possible that at least one of the heaters may be positioned outside the housing to heat the gas and/or product.

The at least one heater may comprise a resistive thermal device or element. The device may include a heat sink to dissipate heat produced by the heater to the product and/or gas.

The heater may be configured to affect the temperature of the product and/or gas by any amount required to perform the desired function. The heater may increase the temperature of the product and/or gas by between about 2 degrees C. and about 30 degrees C. and may preferably increase the temperature of the therapeutic product and/or gas by between about 4 degrees C. and about 10 degrees C. above ambient temperature.

The housing preferably forms at least part of a handheld device which may be held by a user and moved across the skin of a person or animal to apply the product to the skin. The shape and dimensions of the housing are preferably chosen to allow the device to be held by a user's hand and may also allow the fingers of the user to contact the skin. The housing may be arranged or configured to provide a massaging sensation to the skin and/or the manner in which the device is held may allow the user to perform a finger massage to the skin while at the same time using the device.

The product may be selected from any product which may be used to treat the skin, for example a therapeutic product or a cosmetic product. The product is preferably a fluid product and may comprise a lotion or serum. The viscosity of the product and/or gas may be altered following heating by the heater.

The gas preferably comprises a non-toxic gas, such as oxygen, although other non-toxic gases, e.g. nitrogen, or a mixture of gases, such as air, may be used. The gas may be pressurised or unpressurised. The gas may be provided to the device from a separate gas supply. The housing preferably includes a port or other inlet for receiving the gas. The gas may be provided to the housing and/or handheld device from the gas supply by a conduit which may include a tube.

The use of gas can assist in increasing and/or accelerating the absorption of the product into the skin. The heating of the gas and/or product may also assist in increasing and/or accelerating the absorption of the product into the skin.

The device preferably includes a switch that can be actuated by a user to control dispensing the product and/or gas. The switch may cooperate with a valve to dispense the product and/or gas.

The device preferably includes an inlet port for receiving the product. The product may be provided to the device from a container, which may be received in a recess in the device. The container may be a vial or canister. The housing may include a piercing means, such as a sharp protrusion, for piercing the container. The piercing means or protrusion may allow the therapeutic product to be dispensed from the one or more outlets. The piercing means or protrusion is preferably provided on a conduit which is in fluid communication with the one or more outlet when the switch is depressed.

The underside of the housing which, in use, may contact the skin may have an at least partially concave and/or recessed portion. The one or more outlets of the system may be positioned within or around the concave and/or recessed portion of the housing. The gas dispensed from the one or more outlets may provide adequate pressure such that the housing experiences reduced friction against the skin. The gas dispensed from the one or more outlets may allow the housing and/or handheld device to be more easily maneuvered.

DESCRIPTION OF THE DRAWINGS

FIG. 1 is an external perspective view of a device for delivering a product onto the skin of a person or animal with a container of the product according to a first embodiment of the present invention.

FIG. 2 depicts an exploded view of the components of the device of FIG. 1.

FIG. 3a shows a top view of the device of FIG. 1;

FIG. 3b shows a side view of the device of FIG. 1;

FIG. 3c shows an underneath view of the device of FIG. 1;

FIG. 3d shows a section on the line A-A of FIG. 3a;

FIG. 3e shows a section on the line B-B of FIG. 3b;

FIG. 3f shows a section on the line C-C of FIG. 3b;

FIG. 4 is an isometric view of a device for delivering a product onto skin of a person or animal with a container of the product according to a second embodiment of the present invention;

FIG. 5 depicts an exploded view of the components of the device of FIG. 4.

FIG. 6a shows a top view of the device of FIG. 4;

FIG. 6b shows a side view of the device of FIG. 4;

FIG. 6c shows an underneath view of the device of FIG. 4;

FIG. 6d shows a section on the line A-A of FIG. 6b;

FIG. 6e shows a section on the line B-B of FIG. 3b;

FIG. 7 is an isometric view of a device according to another embodiment of the invention.

FIG. 8 is an exploded view of the components of the device of FIG. 7.

FIGS. 9a-9f depict various schematic and cross-sectional views of the device of FIG. 7 as follows:

FIG. 9a shows a top view of the device of FIG. 7;

FIG. 9b shows a side view of the device of FIG. 7;

FIG. 9c shows an underneath view of the device of FIG. 7;

FIG. 9d shows a section on the line A-A of FIG. 9a;

FIG. 9e shows a section on the line B-B of FIG. 7b;

FIG. 9f shows a section on the line C-C of FIG. 3b.

DETAILED DESCRIPTION

Figure 6A:
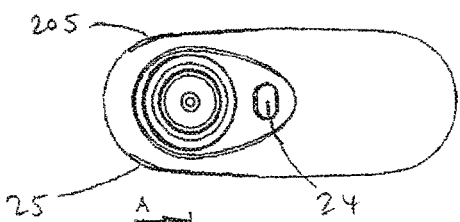
FIGS. 6a-6e depict various schematic and cross-sectional views of the device of FIG. 4 as follows.
Figure 6B:
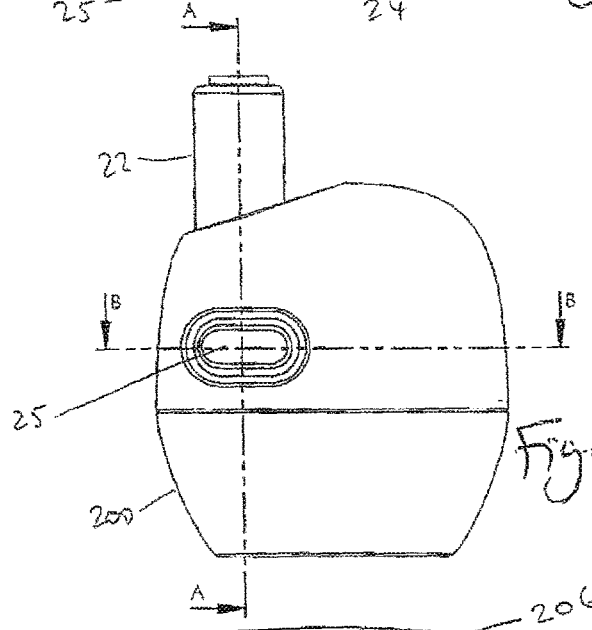
Figure 6D:
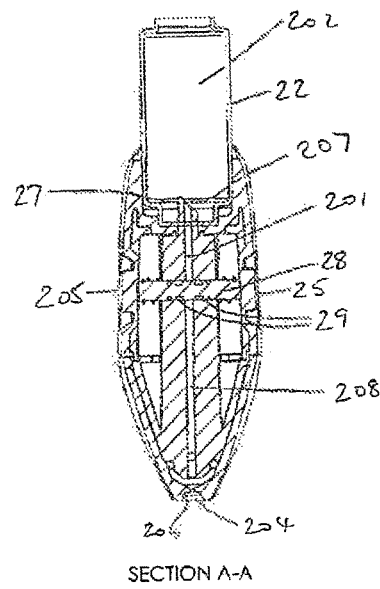

A first embodiment of a hand-held device (10) for delivering a product onto the skin of a person or animal is shown in the isometric view in FIG. 1.

FIG. 1 shows the device (10) comprising a housing (11) and a container (12) for containing a product inserted into a first port (13) of the housing (11). A second port (14) can receive a gas supplied to the system, for example through a tube from a separate gas supply. FIG. 1 shows a first switch (15) which may be user actuated, such as by being pressed by a user's finger or thumb. The housing (11) may be constructed as one piece but more preferably includes a plurality of sections (100, 109) connected together. A lower housing section (100) is shown in FIG. 1 which may be removable to enable parts of the system to be cleaned.

The product which is to be delivered by the system can be selected from any suitable product. The product is preferably a fluid such as a serum or lotion. For example, the product may be a serum or lotion which includes nutrients, vitamins, minerals, chemicals, acids and/or any other active ingredient which can be used to treat the skin in a therapeutic or cosmetic treatment.

The gas to be supplied to the system can be selected from any suitable, non-toxic gas. One preferred embodiment uses oxygen that may be pressurised and supplied from a separate supply. The use of oxygen with the present device can help to increase or accelerate the absorption of the therapeutic product into the skin. It may also be possible to use other gases or combinations of gases with the device to produce a similar effect.

The exterior and interior components of the device are shown in the exploded view of FIG. 2, and the various schematic and sectional views of FIGS. 3a to 3f. The housing (11) comprises an external housing comprising an upper housing section (109) and a lower housing section (100), and an internal housing comprising an upper internal housing section (110) and a lower internal housing section (112). Inside the internal housing is a platform (111) which attaches between the upper internal housing section (110) and the lower internal housing section (112).

The housing (11) may be made of any suitable material, such as a metal or plastics material. In a preferred embodiment the housing (11) is made from a lightweight plastics material.

If cold gas and/or cold product is applied to the skin it can cause a shock or mild distress to a person receiving the treatment. It is therefore desirable to allow the gas and/or product to be heated prior to being dispensed onto the skin. The heated gas and/or product may create a more pleasurable sensation to a person receiving the treatment. For this purpose, a heater (16) is provided within the housing (11).

The heater (16) is preferably a resistive thermal device to which an electrical current is applied. Passing an electrical current through the resistive device causes electrical energy to be converted into heat energy. The heater (16) is preferably mounted on a heat sink (116) formed by the platform (111) which has downwardly disposed fins to dissipate heat to the product and/or gas within the housing. Upon application of a current, the heater (16) and heat sink (116) heat the gas and/or product within the housing (11).

Other types of heater or methods of heating the gas and/or fluid may be used in addition to or in place of the resistive thermal device of the current embodiment. For example the system may make use of an infrared heating device, a convection heater, a heat pump or any other heating device.

FIGS. 1 to 3 show one heater (16) which is positioned within the housing (11). It should be understood that the system may use more than one heating device and still remain within the scope of the invention. The heater (16) may be used to heat the product as well as or instead of the gas. The heater (16) may be positioned at any convenient location within the housing (11) or may be positioned at an external position on or near to the housing, providing the same function of heating the gas and/or product shortly before it is applied takes place.

The heater (16) may be adapted or configured to heat the gas and/or product by any amount necessary. For example, the heater (16) may create enough heat sufficient to increase the temperature of the gas and/or therapeutic product by between 2 degrees to 30 degrees and preferably between 4 degrees to 10 degrees. An embodiment which heats the gas and/or product by less than 2 degrees or more than 30 degrees would still be conceivable within the scope of the invention. The amount by which the gas and/or product is heated would preferably be selected in line with that which would be most comfortable or appealing or effective.

The gas enters the housing (11) through the second port (14) and is heated within the housing (11) by the heater (16). Positioning the heater (16) within the housing (11) allows the gas to be heated closer to being dispensed and lessens the possibility of the gas cooling before it is dispensed. It is possible that the gas could be pre-heated prior to being received at the housing (11), providing it can be dispensed in a heated state to some extent. After being heated, the gas passes into the gas conduit (103) to be dispensed with the product.

The container (12) may be a vial of fluid or any other kind of container such as a canister. The container (12) has an inner reservoir (102) for the fluid product and a lower wall or membrane (107). The container may be disposable once used or may be refillable and reusable. The product may alternatively be supplied to the system by means other than in a container, such as through a tube from a separate reservoir. In the current embodiment the product is released when the wall or membrane (107) of the container (12) is pierced by a protrusion (17) having a sharp edge on a fluid conduit (117) allowing the product contained in the reservoir (102) to flow through an upper channel (101) of the conduit (117). If an alternative method is used for providing the product, it is understood that it may not be necessary for the housing (11) to contain a protrusion (17).

FIGS. 3a-3f show various external and cross-sectional views of the first embodiment of the system. FIG. 3a shows the first switch (15) and a second switch (105), either of which may actuate a spool valve (18) to cause the product to be dispensed when one of the switches (15, 105) is depressed. When one of the switches (15, 105) is depressed a slidable valve member (118) of the valve (18) is displaced such that a groove (19) in the valve member (118) is in line with the upper channel (101) and the lower channel (108). The product may then flow freely through the upper channel (101) and the groove (19) in the valve member (118) through to a lower channel (108) in the fluid conduit (117). Releasing the switch that was depressed will cause the valve member (118) to move back to its original position and thus prevent further release of product. The manner in which the valve is brought back to its original position is not depicted in the figures but may comprise any means such as depressing the opposite switch, or a spring mechanism or other resilient means.

Although the current embodiment is shown using a slidable spool as the valve member (118), it should be understood that any kind of valve may be used to start and/or stop the flow of the product. It is also understood that while the current embodiment uses switches (15, 105) that are user actuated by being depressed, any kind of actuation device may be used to actuate the valve (18). The current embodiment of the invention is provided with two switches (15, 105), but the system may alternatively be provided with only one switch or more than two switches. An alternative mechanism for dispensing the product may not have any actuation means at all and may continue to dispense the product until the reservoir (102) is empty.

When the product passes through the lower channel (108) it reaches an outlet (104) which is provided in a sealing member (113). The sealing member (113) is positioned in the lower exterior of the lower housing section (100). Within the sealing member (113) adjacent to the outlet (104) the product meets the gas which has travelled through a gas conduit (103). The gas collects the product such that the gas and product are projected through the outlet (104). The product and gas then contact the skin to which the device (10) for delivering a product onto human skin is being applied.

The present embodiment of the invention allows the product to be released from the container (12) by gravity acting on the product to send it through the upper channel (101). In the present embodiment this requires the container to be inserted into the upper housing section (109) and/or the upper internal housing section (110). Alternative embodiments which remain within the scope of the current invention may utilise other mechanisms through which the product is released from the container (12), such as by applying a pressure to the product from within the container (12) or by using suction means from the supplied gas to siphon the product out of the container (12). It should be understood that depending on the manner of releasing the product, the arrangement or configuration of the system, including the housing (11) and container (12), may be altered to achieve the desired dispensing of the product.

The lower housing section (100) of the present embodiment is provided with a recessed region (106). When the system is applied to the human skin it is the part of the lower housing section (100) which surrounds the recessed region (106) which contacts the skin. This arrangement allows gas and/or product dispensed from the system and/or air to be contained in the recessed region (106) between the skin and the lower housing section (100). It is possible that the pressure of the gas and/or product dispensed from the system will build up in the recessed region (106). The build up of pressure may act to push the housing (11) at least partially away from the skin. This action may reduce the friction of the lower housing section (100) on the skin and allow a user of the system to more easily manoeuvre the housing over the human skin to which the product is to be applied.

It is a feature of the present embodiment of the invention that the dimensions of the housing (11) are selected such that the housing (11) will be handheld by a user. The housing (11) may be placed in the hand of a user such that one or more finger or thumb of the user can make contact with one or both of the switches (15, 105). It may also be possible for a user to hold the housing (11) in a manner such that one or more finger or thumb of the user can contact the skin, this would allow the user to provide a massage to the skin at the same time as the system provides a therapeutic product to the skin.

Implementation of an alternative embodiment of the device with a plurality of outlets is described below with reference to FIGS. 4-6. In the following description of the embodiment with a plurality of outlets, parts having like reference numerals as those used in the previous section with the first numeral 1 replaced with a first numeral 2 indicate like parts. Unless stated otherwise, these like parts operate substantially in a similar manner to that described above. The device (20) comprises a housing (21) and a container (22) for containing a product. The container (22) is inserted into a first port (13) of the housing (21). A second port (24) can receive a gas supplied to the system. FIG. 5 shows a first switch (25) which may be user actuated, such as by being pressed by a user's finger or thumb. The container (22) may be a vial of fluid or any other kind of container such as a canister.

The exterior and interior components of the device are shown in the exploded view of FIG. 5, and the various schematic and sectional views of FIGS. 6a to 6e. The housing (21) comprises an external housing comprising an upper housing section (209) and a lower housing section (200), and an internal housing comprising an upper internal housing section (210) and a lower internal housing section (212). A partition (211) extends downwardly within the internal housing sections (210) and (212).

The container (22) has an inner reservoir (202) for the fluid product and a lower wall or membrane (207). The container may be disposable once used, or may be refillable and reusable. The product may alternatively be supplied to the system by means other than in a container, such as through a tube from a separate reservoir. A heater (26) is provided within the housing (21). to heat the product and/or the gas prior to being dispensed onto the skin. The heater (16) is preferably a resistive thermal device to which an electrical current is applied. The heater (16) has downwardly disposed fins to dissipate heat to the product and/or gas within the housing.

In the current embodiment the product is released when a wall or membrane (207) of the container (22) is pierced by a protrusion (27) having a sharp edge on a fluid conduit (217) allowing the product contained in the reservoir (202) to flow through an upper channel (201) of the conduit (217). If an alternative method is used for providing the product, it is understood that it may not be necessary for the housing (21) to contain a protrusion (27). The lower housing section (200) of the present embodiment is provided with a recessed region (206). FIG. 6a shows the first switch (25) and a second switch (205), either of which may actuate a spool valve (28) to cause the product to be dispensed when one of the switches (25, 205) is depressed. When one of the switches (25, 205) is depressed a slidable valve member of the valve (28) is displaced such that a groove (29) is in line with the upper channel (201) and the lower channel (208). When the product passes through the lower channel (208) it reaches an outlet (204) which is provided in a sealing member (213). The sealing member (213) is positioned in the lower exterior of the lower housing section (200). Within the sealing member (213) adjacent to the outlet (204) the product meets the gas which has travelled through a gas conduit (203). The gas collects the product such that the gas and product are projected through the outlet (204).

An alternative embodiment depicting a device (20) for delivering a product onto the skin of a person or animal is shown in FIG. 4. This embodiment comprises a handheld device (20) which allows switches (25, 205) to be depressed by one or more finger or thumb of a user, although the position in the hand which the device is held differs from the previous embodiment of FIGS. 1-3. This embodiment does not allow a simultaneous finger massage to be applied as was possible with the embodiment of FIGS. 1-3.

The heater (26) shown in FIG. 5 is configured to be taller in height relative to its width and to occupy an area between the upper internal housing section (210) and the lower internal housing section (212). The heater (26) of this embodiment heats the gas supplied to the housing (21), although it could be alternatively positioned or configured to heat the product.

Figure 6C:
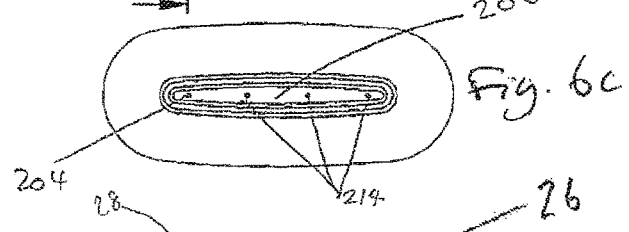
Figure 6E:
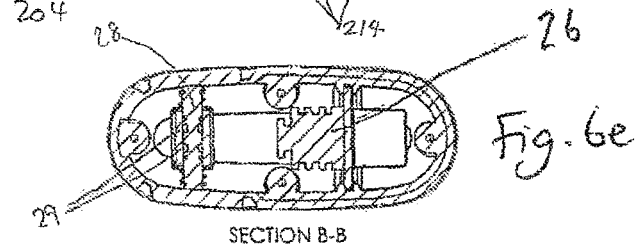

The present embodiment possesses an outlet (204) as shown in FIG. 6c which dispenses the product and gas in a similar manner to the embodiment of FIGS. 1-3. The gas enters the housing (21) through the second port (24) and is heated within the housing (21) by the heater (26). The embodiment also provides three additional outlets (214) which may be configured to allow a percentage of the gas to be dispensed therefrom. It is also possible that further alterations could be made to this embodiment which permit a mixture of the product and the gas to be dispensed through the additional outlets (214).

Another embodiment of a device for delivering a product onto the skin (20) of a person or animal is shown in FIGS. 7, 8 and 9a-9f. This embodiment also comprises a handheld device which is generally similar to the embodiment of FIGS. 1 to 3.

The device (70) of FIGS. 7, 8 and 9a-9f differs from that of FIGS. 1 to 3 in the external shape of the device housing (71) and the container (72) for the product to be dispensed, and also in the form and arrangement of the interior components of the device (70) as will be explained below.

The housing (71) of the device (70) includes an upper external housing section (709) and a lower housing section (700) which, when attached together provide an external shape which is like a boot, whereas the shape of the housing (11) of FIGS. 1 to 3 is more pebble-like. Unlike the device (10) of FIGS. 1 to 3 which has two switches (15 and 105), the device (70) has a single switch (75) located on one side of the housing (71) for use by a right handed person, though it is envisaged that the housing (71) could be modified so that the switch (75) is on the opposite side of the housing for use by a left handed person.

The container (72) for the product to be dispensed has a bulbous-shaped upper portion (721) and a tubular lower portion (722) which is inserted into a recessed first inlet port (73) in the housing (70). This allows a greater volume of product to be contained within the container (72) for a given height than the cylindrical container of FIGS. 1 to 3.

The container (72) has an inner reservoir (702) for the fluid product with a lower wall or membrane (707). The container may be disposable once used or may be refillable and reusable. The product may alternatively be supplied to the system by means other than in a container, such as through a tube from a separate reservoir. In the embodiment of FIGS. 7 to 9, the product is released when the wall or membrane (707) of the container (72) is pierced by a protrusion (77) having a sharp edge on a fluid conduit member (717) allowing the product contained in the reservoir (702) to flow through an upper fluid channel (701) in the conduit member. If an alternative method is used for providing the product, it is understood that it may not be necessary for the conduit member (717) to have a sharp-edged protrusion (77). As shown in FIGS. 9d-9f, the lower part of the fluid conduit member (717) also has a lower fluid channel (708) and a gas conduit (703).

The exterior and interior components of the device (70) are shown in the exploded view of FIG. 8. The housing (71) comprises an external housing comprising an external upper housing section (709) and an external lower housing section (700), and an internal housing comprising an upper internal housing section (710) and a lower internal housing section (712). Inside the internal housing is a platform (711) which attaches between the upper internal housing section (710) and the lower internal housing section (712). A second inlet port (74) is also provided in the upper external and internal housing sections (709, 710) to receive a gas supplied to the device.

The housing (71) may be made of any suitable material, such as a metal or plastics material. In a preferred embodiment the housing (71) is made from a lightweight plastic material.

As with the previous embodiments, a heater (76) is provided within the housing (71) to allow the gas and/or product to be heated prior to being dispensed onto the skin. The heated gas and/or product may create a more pleasurable sensation to a person receiving the treatment.

The heater (76) is preferably a resistive thermal device to which an electrical current is applied. Passing an electrical current through the resistive device causes electrical energy to be converted into heat energy. The heater (76) is mounted on the platform (711), which is preferably made of metal so that it acts as a heat sink to dissipate heat to the product and/or gas within the housing. Upon application of a current, the heater (16) and platform (711) heat the gas and/or product within the housing (11).

As shown in FIG. 8, the platform (711) is smaller than the platform (111) of the device (10), and is mounted on the upper peripheral surface (731) of a compartment (730) in the interior lower housing section (712) by means of a mounting ring (733) and fixing screws (not shown).

The gas enters the housing (71) through the second port (74), and passes into the compartment (730) through an aperture (734) in the platform (711) where it is heated within the compartment (730) by the heater (76) and metal platform (711). Positioning the heater (16) within the compartment (730) allows the gas to be heated closer to being dispensed and lessens the possibility of the gas cooling before it is dispensed. It is possible that the gas could be pre-heated prior to being received at the housing (71), providing it can be dispensed in a heated state to some extent. After being heated, the gas passes into the gas conduit (703) to be dispensed with the product.

FIGS. 9a-9f show various external and cross-sectional views of the first embodiment of the system. FIGS. 9a and 9e show the switch (75) which can actuate a valve (78) to cause the product to be dispensed. When the switch (75) is depressed a slidable valve member (718) of the valve (78) is displaced such that a groove (79) in the valve member (718) is in line with the upper channel (701) and a lower channel (708) in the fluid conduit member (717). The product may then flow freely through the upper channel (701) and the groove (79) in the valve (78) through to a lower channel (708). Releasing the switch (75) will cause the valve (18) to move back to its original position and thus prevent further release of product. The manner in which the valve is brought back to its original position is not depicted in the figures but may comprise any means such as a spring mechanism or other resilient means.

Although the current embodiment is shown using a slidable spool as the valve member (718), it should be understood that any kind of valve may be used to start and/or stop the flow of the product. When the product passes through the lower channel (708) it reaches the outlet (704) which is provided in a sealing member (713). The sealing member (713) is positioned in the lower exterior housing section (700). Within the sealing member (713) adjacent to the outlet (704) the product meets the gas which has travelled through the gas conduit (703). The lower end of the fluid conduit member (717) and the sealing member (713) are so arranged that the heated gas leaving the gas conduit (717) collects the product leaving the lower channel in a type of venturi effect such that the gas and product are projected through the outlet (704). The product and gas then contact the skin to which the device (70) for delivering a product onto human skin (10) is being applied.

The lower housing section (700) of the device (70) is provided with a recessed region (706). At least one rib (714) extends downwardly from the lower surface of the lower housing section (700) to define a part (715) of the recessed region for containing the product and gas/air dispensed from the device between the skin and the lower housing section (700). In the device of FIGS. 1-3, which has a larger recessed region (106) which contains the product and gas/air dispensed from the device, the build up of pressure of the gas/air in the recessed region (106) may act to push the housing (11) at least partially away from the skin. While this action may reduce the friction of the lower housing section (100) on the skin, it can result in an unpleasant sound as the gas/air escapes from the recessed region (106). It has been found that by providing at least one rib (714) within the recessed region (706) in the device of FIGS. 7 to 9, this sound can be reduced. FIG. 9c shows a single continuous rib (714), but it will be appreciated that two or more ribs may be provided within the recessed region (706). Another way of reducing this problem is to provide at least one notch (716) in the lower surface of the lower housing section (700) on at least one side of the recessed region (706) to provide a more controlled escape of air, as shown in FIGS. 7, 9c and 9d.

Preferred embodiments of the invention have been described by way of example only and modifications may be made thereto without departing from the scope of the invention.

Comprises/comprising and grammatical variations thereof when used in this specification are to be taken to specify the presence of stated features, integers, steps or components or groups thereof, but do not preclude the presence or addition of one or more other features, integers, steps, components or groups thereof.

The invention claimed is:

1. A device for applying a fluid product onto skin, the device comprising:
    a housing for receiving the fluid product and a gas;
    an outlet in said housing through which the fluid product and gas are dispensed onto an area of the skin;
    a fluid conduit through which the fluid product passes to the outlet;
    a gas conduit through which the gas passes to the outlet; and
    at least one heater positioned within the housing and arranged or configured to heat the fluid product, and to heat the gas before the heated gas passes into the gas conduit,
    wherein the fluid product meets the gas adjacent to the outlet where the heated gas collects the fluid product such that the heated gas and fluid product are projected together and dispensed through the outlet, and the gas and fluid product are applied to the skin in a heated state,
    wherein the outlet is provided in a sealing member positioned in the lower exterior of the housing, wherein the fluid product meets the heated gas within the sealing member adjacent to the outlet; and
    wherein a section of the housing is configured to contact the skin in use and be moved across the skin as the fluid product is applied.

2. The device according to claim 1, wherein the housing forms at least part of a handheld device.

3. A device according to claim 2, wherein, in use, the handheld device is configured to be held by a user's hand with the fingers of the user in contact with the skin.

4. A device according to claim 1, wherein the housing is arranged or configured to provide a massaging sensation to the skin.

5. A device according to claim 1, wherein said heater comprises a resistive thermal device.

6. A device according to claim 1, wherein the device includes a heat sink.

7. A device according to claim 1, wherein the heater is configured to increase the temperature of the fluid product and/or the gas by 2 degrees C. to 30 degrees C. above ambient temperature.

8. A device according to claim 1, wherein the fluid product is a lotion or serum used to treat the skin.

9. A device according to claim 1, wherein the gas comprises a non-toxic gas or mixture of gases or oxygen.

10. A device according to claim 1, wherein the gas is pressurised.

11. A device according to claim 1, wherein the housing comprises an inlet for receiving the gas from a separate supply.

12. A device according to claim 1, wherein the device includes a user actuated switch which cooperates with a valve to allow the fluid product and/or gas to be dispensed.

13. A device according to claim 1, wherein the device includes an inlet port for receiving the fluid product.

14. A device according to claim 13 wherein the housing includes a recess adjacent the inlet port for receiving a container containing the fluid product.

15. A device according to claim 14 wherein the device includes a piercer for piercing the container containing the fluid product.

16. A system according to claim 15, wherein the device includes a user actuated switch which cooperates with a valve to allow the fluid product and/or gas to be dispensed, and the piercer is provided on a conduit in fluid communication with the outlet when the switch is depressed.

17. A device according to claim 1, wherein the section of the housing which contacts the skin is an underside of the housing which has an at least partially concave and/or recessed portion.

18. A device according to claim 17, wherein at least one rib extends downwardly from the underside of the housing within the concave or recessed portion of the section of the housing.

19. A device according to claim 17, wherein at least one notch is provided in a lower surface of the housing on at least one side of the concave or recessed portion.

20. A device according to claim 1, wherein the gas dispensed from the housing provides adequate pressure between the skin and the housing such that the housing can be more easily maneuvered.

* * * * *